United States Patent
Fu et al.

(10) Patent No.: US 11,634,382 B2
(45) Date of Patent: Apr. 25, 2023

(54) PROCESS OF PREPARING 3-FLUORO-5(((1R,2AR)-3,3,4,4-TETRAFLUORO-1,2A-DIHYDROXY-2,2A,3,4-TETRAHYDRO-1H-CYCLOPENTA[CD]INDEN-7-YL)-OXY) BENZONITRILE

(71) Applicant: NiKang Therapeutics, Inc., Wilmington, DE (US)

(72) Inventors: Jiping Fu, Danville, CA (US); Yan Lou, Dallas, TX (US); Yigang He, Newark, DE (US); Yuetao Shi, Changzhou (CN); Peng Zhou, Suzhou Industrial Park (CN); Xingxing Li, Changzhou (CN)

(73) Assignee: NiKang Therapeutics, Inc., Wilmington, DE (US)

( * ) Notice: Subject to any disclaimer, the term of this patent is extended or adjusted under 35 U.S.C. 154(b) by 0 days.

(21) Appl. No.: 17/503,176

(22) Filed: Oct. 15, 2021

(65) Prior Publication Data

US 2022/0119345 A1    Apr. 21, 2022

(51) Int. Cl.

| | |
|---|---|
| *C07C 253/30* | (2006.01) |
| *C07C 29/143* | (2006.01) |
| *C07C 45/27* | (2006.01) |
| *C07C 45/66* | (2006.01) |
| *C07C 67/307* | (2006.01) |
| *C07C 29/00* | (2006.01) |
| *C07C 45/00* | (2006.01) |
| *C07C 67/343* | (2006.01) |

(52) U.S. Cl.
CPC ............ *C07C 253/30* (2013.01); *C07C 29/00* (2013.01); *C07C 29/143* (2013.01); *C07C 45/002* (2013.01); *C07C 45/27* (2013.01); *C07C 45/66* (2013.01); *C07C 67/307* (2013.01); *C07C 67/343* (2013.01); *C07C 2602/08* (2017.05); *C07C 2603/10* (2017.05)

(58) Field of Classification Search
CPC ... C07C 253/30; C07C 29/143; C07C 45/002; C07C 45/27; C07C 45/66; C07C 67/307
See application file for complete search history.

(56) References Cited

U.S. PATENT DOCUMENTS

2020/0361855 A1    11/2020   Fu et al.

FOREIGN PATENT DOCUMENTS

| CN | 104058935 A | 9/2014 |
|---|---|---|
| JP | 2008001631 A | 1/2008 |
| WO | WO 2015/035223 A1 | 3/2015 |
| WO | WO 2018/031680 A | 2/2018 |
| WO | WO 2020/081695 A1 | 4/2020 |
| WO | WO 2020/214853 A | 10/2020 |
| WO | WO 2021/016280 A1 | 1/2021 |
| WO | WO 2021/212062 A1 | 10/2021 |
| WO | WO 2022/086822 A1 | 4/2022 |

OTHER PUBLICATIONS

International Search Report and Written Opinion of PCT/CN2020/121780 dated Jul. 29, 2021; 13 pages.
International Search Report and Written Opinion of PCT/CN2021/055295 dated Jan. 31, 2022; 12 pages.
Barnett et al., "The Mechanism and an Improved Asymmetric Allylboration of Ketones Catalyzed by Chiral Biphenols", Angew. Chem. Int. Ed. 2009, vol. 48, pp. 8679-8682; DOI: 10.1002/anie.200904715.

*Primary Examiner* — Sikarl A Witherspoon
(74) *Attorney, Agent, or Firm* — Squire Patton Boggs (US) LLP

(57) ABSTRACT

Disclosed herein are processes for preparing certain intermediates useful in the synthesis of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile or a pharmaceutically acceptable salt thereof.

37 Claims, No Drawings

PROCESS OF PREPARING 3-FLUORO-5(((1R,2AR)-3,3,4,4-TETRAFLUORO-1,2A-DIHYDROXY-2,2A,3,4-TETRAHYDRO-1H-CYCLOPENTA[CD]INDEN-7-YL)-OXY) BENZONITRILE

CROSS-REFERENCE TO RELATED APPLICATIONS

This application is a U.S. Nonprovisional Application claims the benefit of PCT International Application No. PCT/CN2020/121780, filed on Oct. 19, 2020, the entire contents of which are hereby incorporated by reference in their entirety.

FIELD OF THE DISCLOSURE

Disclosed herein are processes for preparing certain intermediates useful in the synthesis of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile (hereinafter Compound (I)) having the structure:

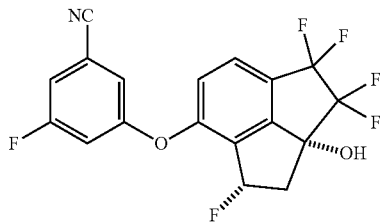

or a pharmaceutically acceptable salt thereof.

BACKGROUND

Compound (I) is a hypoxia inducible factor-2α (HIF-2α) inhibitor and is being developed for treating diseases mediated by aberrant activity of HIF-2α including cancer, such as renal cancer, glioblastoma, neuroblastoma, pheochromocytomas and paragangliomas, somatostatinomas, hemangioblastomas, gastrointestinal stromal tumors (GIST), pituitary tumors, leiomyomas, leiomyosarcomas, polycythaemia, and retinal tumors and non-cancer diseases such as pulmonary artery hypertension (PAH), reflux esophagitis, hepatic steatosis, NASH, inflammatory disease such as inflammatory bowel disease, autoimmune disease such as Graft-versus-Host-Disease, and iron overload.

Synthesis of Compound (I) is disclosed in Example 5 of PCT Application No. Publication No. WO 2020/214853, filed on Apr. 16, 2020. There is a need for alternative processes that allow for large scale synthesis of Compound (I) in a cost-effective manner. The processes disclosed herein fullfill this and related needs.

SUMMARY

Provided herein is a process for preparing 3-fluoro-5-(1R,2aR)-3,3,4,4-tetrafluoro-1,2a-dihydroxy-2,2a,3,4-tetrahydro-1H-cyclopenta[cd]inden-7-yl)oxy)-benzonitrile (hereinafter compound 11) having the structure:

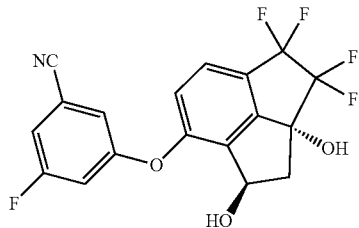

that makes it feasible to produce Compound (I) in high purity, including enantiomeric purity, and yield in a cost-effective manner and that is suitable for use in the preparation of Compound (I) on a commercial scale. Also, provided are processes for preparing certain intermediates used in such process.

In one aspect, provided is a process of preparing compound (11):

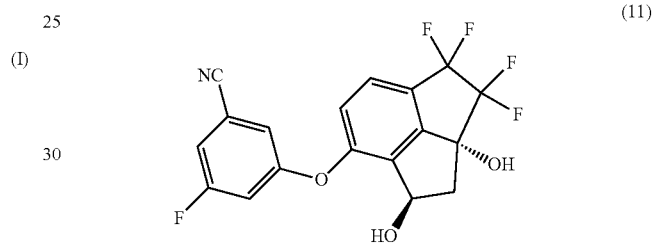

comprising reducing the keto moiety of compound (10):

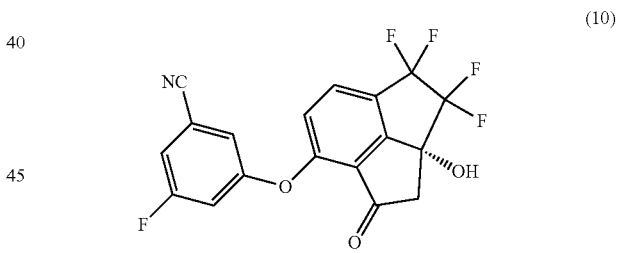

with a suitable reducing agent in a suitable organic solvent; and optionally in the presence of an organic acid.

In a second aspect, provided is a process of preparing compound (10):

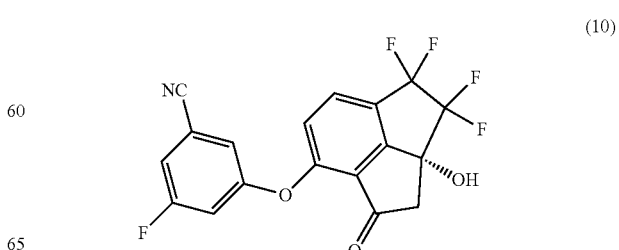

comprising reacting compound (9):

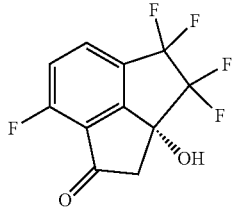
(9)

with 3-fluoro-5-hydroxybenzonitrile in the presence of a base in a suitable organic solvent.

In a third aspect, the process of the first aspect, further comprising preparing compound (10):

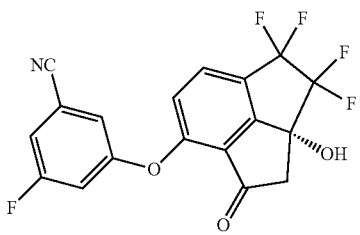
(10)

by reacting compound (9):

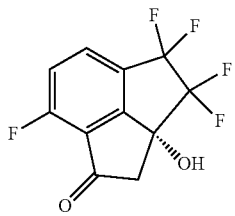
(9)

with 3-fluoro-5-hydroxybenzonitrile in the presence of a base in a suitable organic solvent.

In a fourth aspect, provided is a process for preparing compound (9):

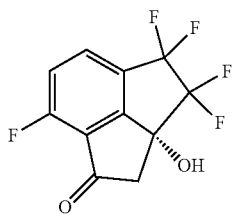
(9)

comprising carrying out oxidative cleavage of the vinylidene moiety of compound (8):

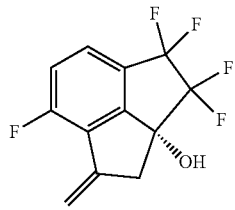
(8)

with a suitable oxidizing agent in a suitable organic or aqueous organic solvent.

In a fifth aspect, the processes of the second and third aspects, further comprise preparing compound (9):

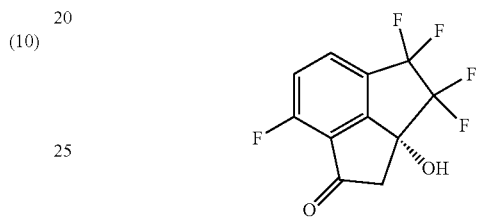
(9)

by carrying out oxidative cleavage of the vinylidene moiety of compound (8):

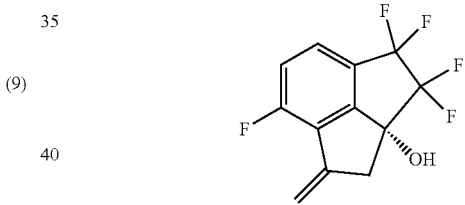
(8)

with a suitable oxidizing agent in a suitable organic or aqueous organic solvent.

In a sixth aspect, provided is a process for preparing compound (8):

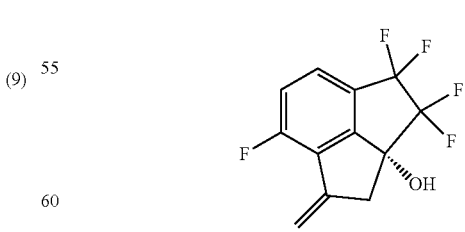
(8)

comprising performing intramolecular cyclization between the alkene and bromo groups in compound (7):

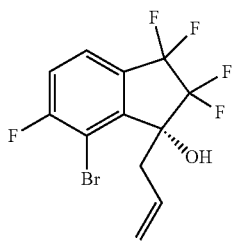

(7)

by treating compound (7) with a palladium catalyst in the presence of a base in a suitable organic or aqueous organic solvent.

In a seventh aspect, the processes of the fourth and fifth aspects, further comprise preparing compound (8):

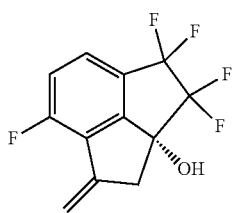

(8)

by performing intramolecular cyclization between the alkene and bromo groups in compound (7):

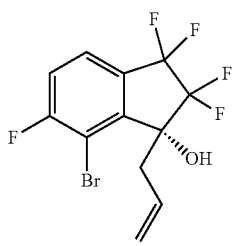

(7)

with a palladium catalyst in the presence of a base in a suitable organic or aqueous organic solvent.

In an eighth aspect, provided is a process for preparing compound (7):

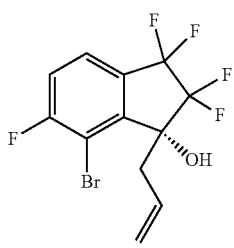

(7)

comprising brominating compound (6):

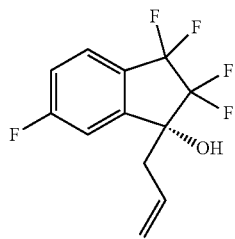

(6)

with a brominating agent in the presence of a deprotonating agent in a suitable organic solvent.

In a ninth aspect, the processes of the sixth and seventh aspects, further comprise preparing compound (7):

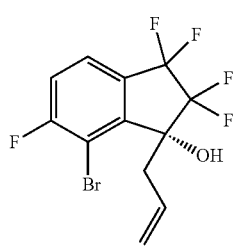

(7)

by treating compound (6):

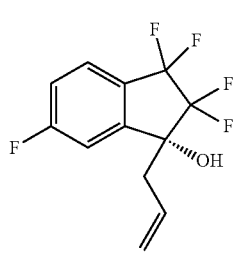

(6)

with a brominating agent in the presence of a deprotonating agent in a suitable organic solvent.

In a tenth aspect, the processes of the eighth and ninth aspects, further comprise preparing compound (6):

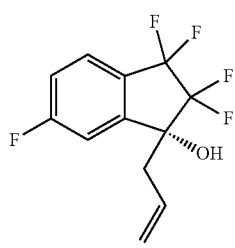

(6)

by treating compound (5):

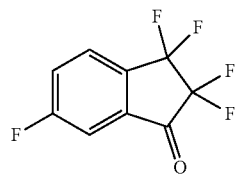
(5)

with 4,4,5,5-tetramethyl-2-(prop-2-en-1-yl)-1,3,2-dioxaborolane in the presence of (S)-2-((3-(tert-butyl)-2-hydroxybenzyl)amino)-N,N,3-trimethylbutanamide and a base in a suitable organic solvent.

In an eleventh aspect, the process of tenth aspect, further comprises preparing compound (5):

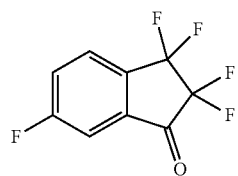
(5)

by treating compound (4):

(4)

with an organolithium reagent in a suitable organic solvent.

In a twelfth aspect, the process of eleventh aspect, further comprises preparing compound (4):

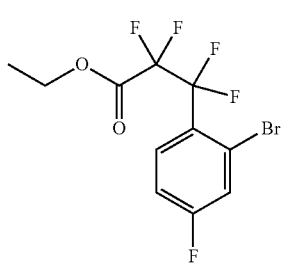
(4)

by treating compound (3):

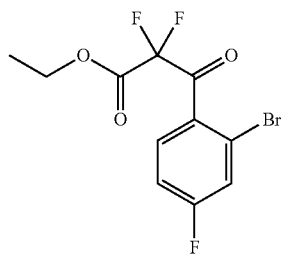
(3)

with a fluorinating agent in a suitable organic solvent.

In a thirteenth aspect, the process of twelfth aspect, further comprises preparing compound (3):

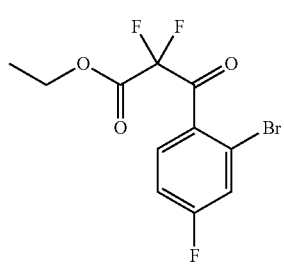
(3)

by treating compound (2):

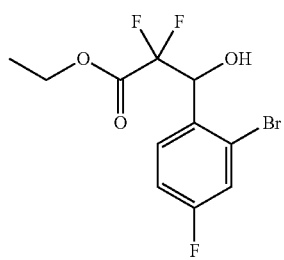
(2)

with an oxidizing agent in a suitable organic solvent.

In a fourteenth aspect, the process of thirteenth aspect, further comprises preparing compound (2):

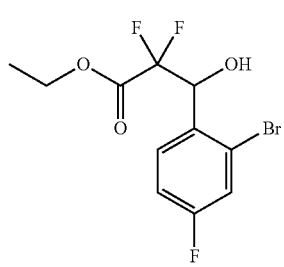
(2)

by treating compound (1):

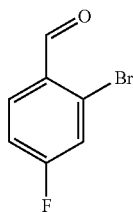

(1)

with ethyl 2-bromo-2,2-difluoroacetate in the presence of zinc metal, trimethylsilyl chloride, and 1,2-dibromoethane in a suitable organic solvent.

DETAILED DESCRIPTION

Definitions

Unless otherwise stated, the following terms used in the specification and claims are defined for the purposes of this Application and have the following meaning:

As used herein, the term "reacting" or "treating" when describing a certain process is used as known in the art and generally refers to the bringing together of chemical reagents in such a manner so as to allow their interaction at the molecular level to achieve a chemical or physical transformation. The reacting steps of the processes described herein can be conducted for a time and under conditions suitable for preparing the identified product.

"Suitable organic solvent" refers to an organic solvent which, under the reaction conditions of the processes disclosed herein, does not enter into any appreciable reaction with either the reactants, intermediates an/or the products at the temperatures at which the reactions are carried out. A given reaction disclosed herein can be carried out in one organic solvent or a mixture of two or more organic solvents. Examples of suitable organic solvents that can be used in the reactions described herein include: halogenated solvents such as carbon tetrachloride, chloroform, dichloromethane, and the like; ethers such as tetrahydrofuran, 2-methyltetrahydrofuran, 1,3-dioxane, 1,4-dioxane, diethyl ether, methyl t-butyl ether, and the like; alcohols such as methanol, ethanol, 1-propanol, 2-propanol, 1-butanol, 2-butanol, n-butyl alcohol, tert-butyl alcohol, 1-, 2-, or 3-pentanol, neo-pentyl alcohol, and the like; hydrocarbons such as benzene, toluene, xylene, cyclohexane, pentane, hexane, heptane, and the like. Additional organic solvents that can be used in the reactions described herein include polar organic solvents including, but not limited to, acetonitrile, dimethylformamide, ethyl acetate, alcohols, and the like. Examples of suitable organic solvents that can be used in the reactions described herein include: halogenated solvents such as carbon tetrachloride, chloroform, dichloromethane, 1,2-dichloroethane, and the like; ethers such as tetrahydrofuran, 2-methyltetrahydrofuran, 1,3-dioxane, 1,4-dioxane, diethyl ether, methyl t-butyl ether, and the like; alcohols such as methanol, ethanol, 1-propanol, 2-propanol, 1-butanol, 2-butanol, n-butyl alcohol, tert-butyl alcohol, 1-, 2-, or 3-pentanol, neo-pentyl alcohol, and the like; aromatic hydrocarbons such as benzene, toluene, xylene, and the like; alkanes such as cyclohexane, cyclopentane, pentane(s), hexane(s) (including n-hexane), heptane(s) (including n-heptane), isooctane(s) and the like. Additional organic solvents that can be used in the reactions described herein include polar organic solvents including, but not limited to, acetonitrile, dimethylformamide, ethyl acetate, alcohols, and the like. When polar organic solvents (e.g., alcohols, acetonitrile, DMF) contain water they are referred to herein as aqueous organic solvent. Depending on the reaction step, solvents that are suitable for the particular reaction step can be readily selected by a person skilled in the art.

For example, in the preparation of compound (2), besides, THF, the reaction was also carried out in MTBE, 2-methylTHF, or toluene solvent. In the preparation of compound (3), the reaction was also carried out in THF solvent. In the preparation of compound (4), the reaction was also carried out in CHCl$_3$ solvent. In the preparation of compound (5), the reaction was also carried out in 2-methyl THF, n-heptane, or MTBE solvent. In the preparation of compound (8), the reaction was also carried out in DMF, 1,4-dioxane, THF, 2-methyl THF, toluene, or acetonitrile solvent. In the preparation of compound (9), the reaction was also carried out in a mixture of DCM/ACN/water. In the preparation of compound (10), the reaction was also carried out in DMF, ACN, 2-methyl THF, or toluene solvent. In the preparation of compound (11), the reaction was also carried out in THF, CH$_3$OH, TFA/THF, or HOAc/THF solvent.

In addition, the reactions were carried out at various temperatures. Reaction temperatures that were used in the preparation of compound (2) included 20° C., 40° C., 60° C., and refluxing. Reaction temperatures that were used in the preparation of compound (3) included 0-15° C. and 15-25° C. Reaction temperatures that were used in the preparation of compound (4) included 0-10° C., 10-20° C., 20-30° C., and 30-40° C. Reaction temperatures that were used in the preparation of compound (5) included −30 to −40° C., −40 to −50° C., −50 to −60° C., and −60 to −70° C. Reaction temperatures that were used in the preparation of compound (6) included 35° C., 45° C., and 60° C. Reaction temperatures that were used in the preparation of compound (7) included −100 to −80° C., −80 to −60° C., and −60 to −40° C. Reaction temperatures that were used in the preparation of compound (8) included 60° C., 70° C. and refluxing. Reaction temperatures that were used in the preparation of compound (10) included 20 to 30° C., and 40° C. Reaction temperatures that were used in the preparation of compound (11) included 10 to 20° C. and −5 to 5° C.

In addition, the brominating agents that can be used in the preparation of compound (7) herein include bromotrichloromethane, 1,2-dibromo-1,1,2,2-tetrachloroethane, 1,2-dibromo-1,1,2,2-tetrafluoroethane, carbon tetrabromide, N-bromosuccinimide, N-bromophthalimide, N-bromosaccharin, N-bromoacetamide, 1,3-dibromo-5,5-dimethylhydantoin dibromoisocyanuric acid, monosodium bromoisocyanurate, bromodimethylsulfonium, bromide, 5,5-dibromomeldrum's acid, 2,4,4,6-tetrabromo-2,5-cyclohexadienone, bis(2,4,6-trimethylpyridine)-bromonium hexafluorophosphate; and bromine and its equivalents, such as bromine-1,4-dioxane complex, tetrabutylammonium tribromide, trimethylphenylammonium tribromide, benzyltrimethylammonium tribromide, and 1-butyl-3-methylimidazolium tribromide.

Additionally, bases that were used in the preparation of compound (8) included NaOAc, KOAc, and K$_2$CO$_3$;

brominating reagents that were used in the preparation of compound (7) included CBr$_4$ and CF$_2$BrCF$_2$Br;

catalysts that were used in the preparation of compound (8) included Pd(dppf)Cl$_2$, Pd$_2$(dba)$_3$/XPhos, Pd(OAc)$_2$/PPh$_3$, and Pd(PPh$_3$)Cl$_2$;

fluorinating reagents that were used in the preparation of compound (4) included DAST, 4-tert-butyl-2,6-dimethylphenylsulfur trifluoride, and HF/SF$_4$;

oxidizing agents that were used in the oxidation of compound (2) to (3) included 2-iodoxybenzoic acid (IBX), RuCl$_3$/NaBrO$_3$; TEMPO/NaClO, MnO$_2$, and TPAP/NMO.

oxidizing agents that were used in the oxidation of compound (8) to (9) included RuCl$_3$/NaIO$_4$, RuCl$_3$/Oxone® and O$_3$; and reducing agents that were used in the reduction of compound (10) to (11) included LiBH$_4$ and NaBH$_4$.

The reactions of the processes described herein can be carried out in air or under an inert atmosphere. Typically, reactions containing reagents or products that are substantially reactive with air can be carried out using air-sensitive synthetic techniques that are well known to the skilled artisan.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry, or mass spectrometry; or by chromatography such as high performance liquid chromatography (HPLC) or thin layer chromatography. The compounds obtained by the reactions can be purified by any suitable method known in the art. For example, chromatography (medium pressure) on a suitable adsorbent (e.g., silica gel, alumina and the like), HPLC, or preparative thin layer chromatography; distillation; sublimation, trituration, or recrystallization. The purity of the compounds, in general, are determined by physical methods such as measuring the melting point (in case of a solid), obtaining an NMR spectrum, or performing a HPLC separation.

"Cyclic ether" refers to tetrahydrofuran, 2-methyltetrahydrofuran, or 1,4-dioxane.

"Alcohol" refers to an aliphatic hydrocarbon compound that carries a hydroxy group. Representative examples include, but are not limited to, methanol, ethanol, propanol, butanol, and the like.

"About" as used herein means±10%, preferably ±5% of listed value. For example, a reaction carried out at about 10° C. includes 9° C., 11° C., and all temperatures contained in between 9° C. and 11° C.

"A" and "an" as used herein means one or more (in some embodiments, 1, 2, or 3), unless context clearly dictates otherwise. For example, "a suitable organic solvent" or "an organic solvent" includes a single solvent and includes mixture of solvents, unless context clearly dictates otherwise; in the case that a single specific solvent is recited in an embodiment, then "a" and "an" means one.

The reactions of the processes described herein can be carried out in air or under an inert atmosphere. Typically, reactions containing reagents or products that are substantially reactive with air can be carried out using air-sensitive synthetic techniques that are well known to the skilled artisan.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry, or mass spectrometry; or by chromatography such as high performance liquid chromatography (HPLC) or thin layer chromatography. The compounds obtained by the reactions can be purified by any suitable method known in the art. For example, chromatography (medium pressure) on a suitable adsorbent (e.g., silica gel, alumina and the like), HPLC, or preparative thin layer chromatography; distillation; sublimation, trituration, or recrystallization. The purity of the compounds, in general, are determined by physical methods such as measuring the melting point (in case of a solid), obtaining an NMR spectrum, or performing a HPLC separation.

EMBODIMENTS

1A. In embodiment 1A, the process of preparing compound (11):

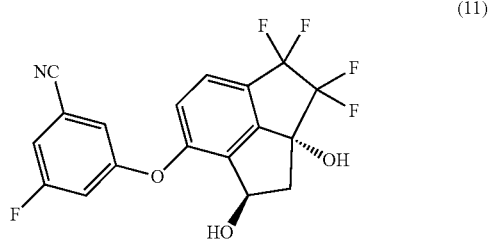 [SMILES: N#Cc1cc(F)cc(Oc2ccc3c4c2[C@H](O)C[C@]4(O)C(F)(F)C3(F)F)c1]

is as described in the first aspect of the Summary.

1B. In embodiment 1B, the process of embodiment 1A is wherein the reducing agent is sodium borohydride, lithium borohydride, sodium acetoxy borohydride, or sodium cyanoborohydride.

1. In embodiment 1, the process of preparing compound (11):

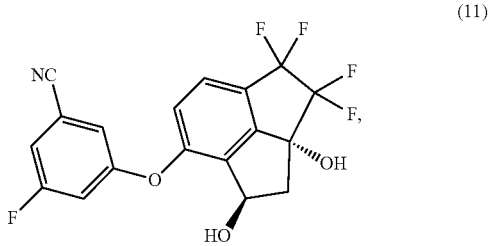

according to embodiment 1A comprises reducing the keto moiety of compound (10):

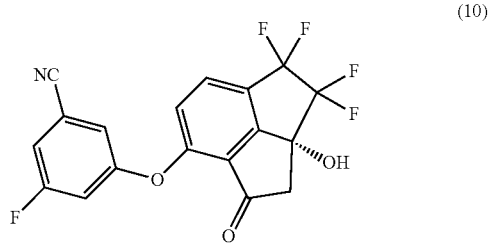 [SMILES: N#Cc1cc(F)cc(Oc2ccc3c4c2C(=O)C[C@]4(O)C(F)(F)C3(F)F)c1]

with:

(a) sodium borohydride in an organic solvent selected from the group consisting of (i) an alcohol containing acetic acid or trifluoroacetic acid, (ii) a cyclic ether, and (iii) a mixture of a cyclic ether and an alcohol; wherein the cyclic ether of (ii) and the mixture of a cyclic ether and an alcohol of (iii) optionally contain acetic acid or trifluoroacetic acid; or (b) lithium borohydride in a suitable organic solvent optionally containing acetic acid or trifluoroacetic acid.

2. In embodiment 2, the process of embodiment 1A, 1B, or 1 is wherein the reduction of the keto group of compound

(10) is carried out with sodium borohydride in tetrahydrofuran, 2-methyltetrahydrofuran, a mixture of tetrahydrofuran or 2-methyltetrahydrofuran and methanol, tetrahydrofuran containing acetic acid or trifluoroacetic acid, 2-methyltetrahydrofuran containing acetic acid or trifluoroacetic acid, or methanol containing acetic acid or trifluoroacetic acid.

3. In embodiment 3, the process of embodiment 2 is wherein the organic solvent is a mixture of tetrahydrofuran and methanol and the reaction is carried out at about −5° C. to about 30° C.

4. In embodiment 4, the process of embodiment 2 is wherein the organic solvent is a mixture of tetrahydrofuran and methanol and the reaction is carried out at about −5° C. to about 5° C.

5A. In embodiment 5A, the process of preparing compound (10):

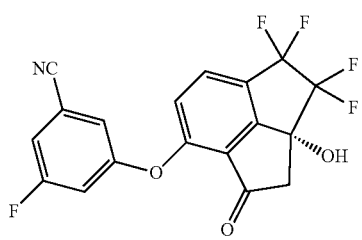

is as described in the second aspect in the Summary.

5. In embodiment 5, the process of embodiment 5A comprises reacting compound (9):

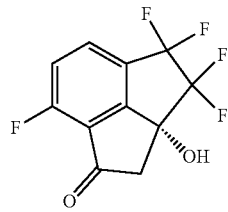

with 3-fluoro-5-hydroxybenzonitrile in the presence of a base in a suitable organic solvent other than dimethylformamide.

6. In embodiment 6, the process of any one of embodiments 1A to 4, further comprising preparing compound (10):

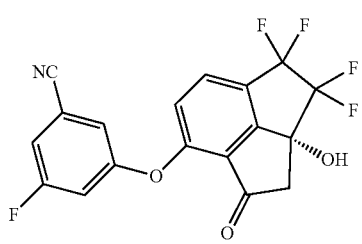

by reacting compound (9):

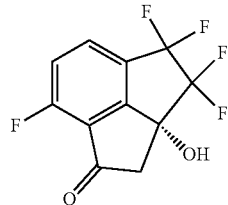

with 3-fluoro-5-hydroxybenzonitrile in the presence of a base in a suitable organic solvent.

7. In embodiment 7, the process of embodiment 5A, 5 or 6 is wherein the base is an inorganic base.

8. In embodiment 8, the process of embodiment 7 is wherein the inorganic base is cesium carbonate or potassium carbonate 9. In embodiment 9, the process of any one of embodiments 5A and 6 to 8 is wherein the organic solvent is tetrahydrofuran, 2-methyltetrahydrofuran, dimethylformamide, acetonitrile, or toluene.

10. In embodiment 10, the process of embodiment 9 is wherein the organic solvent is tetrahydrofuran.

11. In embodiment 11, the process of any one of embodiments 5A to 10 is wherein the reaction is carried out at about 20° C. to about 40° C.

12. In embodiment 12, the process of any one of embodiments 5A to 11, further comprising crystallizing compound (10) from a mixture of an ether and an alkane solvent.

13. In embodiment 13, the process of embodiment 12 is wherein compound (10) is crystallized from a mixture of methyl tert-butyl ether and n-heptane.

14A. In embodiment 14A, provided is a process for preparing compound (9):

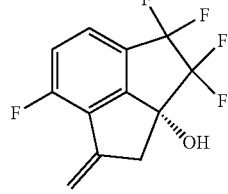

as described in the fourth embodiment of the Summary.

14. In embodiment 14, the process of embodiment 14A comprises carrying out oxidative cleavage of the vinylidene moiety of compound (8):

with (i) sodium periodate in the presence of ruthenium chloride in aqueous acetonitrile, (ii) Oxone in the presence of ruthenium chloride in a suitable organic or aqueous organic solvent, or (iii) Ozone in a suitable organic or aqueous organic solvent.

15. In embodiment 15, the process of any one of embodiments 5A to 13, further comprising preparing compound (9):

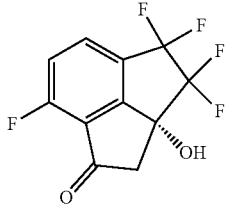
(9)

by carrying out oxidative cleavage of the vinylidene moiety of compound (8):

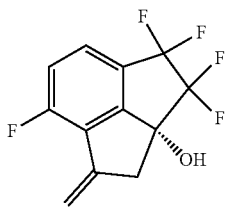
(8)

with a suitable oxidizing agent in a suitable organic or aqueous organic solvent.

16. In embodiment 16, the process of embodiment 15 is wherein the oxidative cleavage of the vinylidene is carried out with (i) sodium periodate or Oxone in the presence of ruthenium chloride or (ii) Ozone.

17. In embodiment 17, the process of any one of embodiments 14A to 16 is wherein the solvent is a mixture of dichloromethane, acetonitrile, and water or the solvent is aqueous acetonitrile.

18. In embodiment 18, the process of any one of embodiments 14A to 17 is wherein the oxidative cleavage of the vinylidene is carried out with sodium periodate in the presence of catalytic amount of ruthenium chloride in aqueous acetonitrile.

19. In embodiment 19, the process of any one of embodiments 14A to 18, further comprising purification of compound (9) from a mixture of an ether and an alkane solvent.

20. In embodiment 20, the process of embodiment 19 is wherein purification of compound (9) is from a mixture of methyl tert-butyl ether and n-heptane. 21A. In embodiment 21A, provided is a process for preparing compound (8):

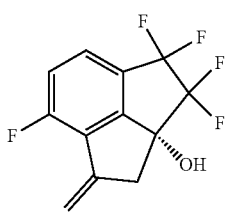
(8)

is as defined in the sixth aspect of the Summary.

21. In embodiment 21, the process of embodiment 21A comprises performing intramolecular cyclization between the alkene and bromo groups in compound (7):

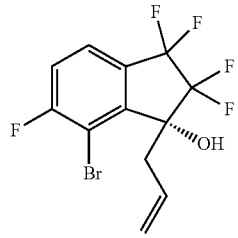
(7)

by treating compound (7) with a palladium catalyst in the presence of a base in a suitable organic solvent other than dimethylformamide.

22. In embodiment 22, the process of any one of embodiments 14A to 20, further comprising preparing compound (8):

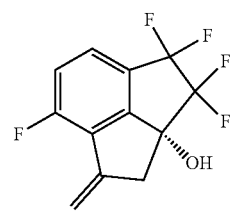
(8)

by performing intramolecular cyclization between the alkene and bromo groups in compound (7):

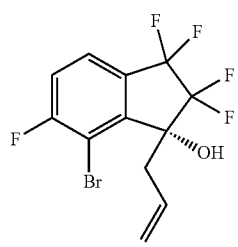
(7)

with a palladium catalyst in the presence of a base in a suitable organic solvent.

23. In embodiment 23, the process of embodiment 21A, 21 or 22 is wherein the palladium catalyst is Pd(PPh$_3$)$_4$, Pd(dppf)Cl$_2$, Pd(PPh$_3$)$_2$Cl$_2$, Pd(PPh$_3$)$_2$(OAc)$_2$, Pd$_2$(dba)$_3$/XPhos, or Pd(1,2-bis(diphenylphosphino)ethane)(OAc)$_2$, and the organic solvent is acetonitrile, tetrahydrofuran, 2-methyltetrahydrofuran, toluene, 1,4-dioxane, or dimethylformamide.

24. In embodiment 24, the process of embodiment 23 is wherein the base is sodium acetate, potassium acetate, sodium carbonate, potassium carbonate, or cesium carbonate.

25. In embodiment 25, the process of any one of embodiments 21A, 21, 22, or 24 is wherein the palladium catalyst is Pd(PPh$_3$)$_2$Cl$_2$, the base is potassium acetate, and the solvent is acetonitrile.

26. In embodiment 26, the process of embodiment 25 is wherein the reaction is carried out between about 60° C. to about 80° C.

27A. In embodiment 27A, provided is a process for preparing compound (7):

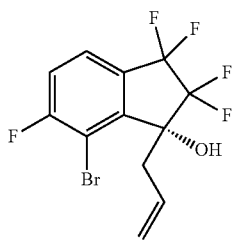 (7)

is as described in the eighth aspect of the Summary.

27. In embodiment 27, the process of embodiment 27A comprises brominating compound (6):

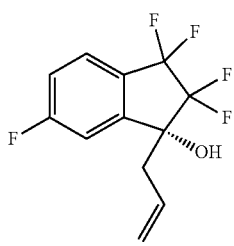 (6)

with 1,2-dibromo-1,1,2,2-tetrafluoroethane in the presence of a deprotonating agent in a suitable organic solvent.

28. In embodiment 28, the process of any one of embodiments 21A to 26, further comprising preparing compound (7):

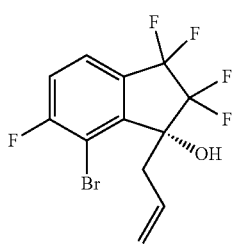 (7)

by treating compound (6):

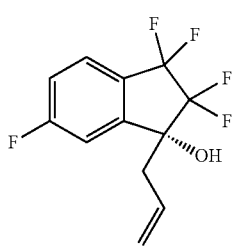 (6)

with a brominating agent in the presence of a deprotonating agent in a suitable organic solvent.

29. In embodiment 29, the process of embodiment 28 is wherein the brominating agent is carbon tetrabromide or 1,2-dibromo-1,1,2,2-tetrafluoroethane.

30. In embodiment 30, the process of embodiment 27A, 27 or 28 is wherein the brominating agent is 1,2-dibromo-1,1,2,2-tetrafluoroethane, the deprotonating agent is lithium diisopropylamide and the solvent is tetrahydrofuran.

31. In embodiment 31, the process of embodiment 30 is wherein the reaction is carried at out at about −100° C. to about −20° C.

32. In embodiment 32, the process of any one of embodiments 27A, 27 and 28 to 31, further comprising preparing compound (6):

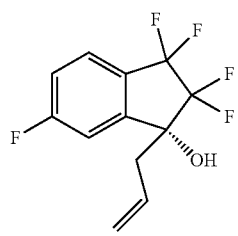 (6)

by treating compound (5):

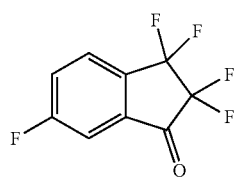 (5)

with 4,4,5,5-tetramethyl-2-(prop-2-en-1-yl)-1,3,2-dioxaborolane in the presence of (S)-2-((3-(tert-butyl)-2-hydroxybenzyl)amino)-N,N,3-trimethylbutanamide and a base in a suitable organic solvent.

33. In embodiment 33, the process of embodiment 32 is wherein the base is sodium tert-butoxide and the organic solvent is a mixture of methanol and toluene.

34. In embodiment 34, the process of claim 32 or 33, further comprising preparing compound (5):

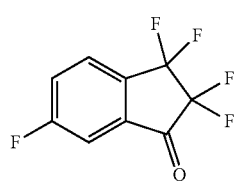 (5)

by treating compound (4):

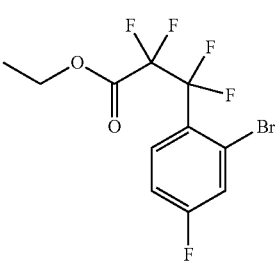 (4)

with an organolithium reagent in a suitable organic solvent.

35. In embodiment 35, the process of claim 34 is wherein the organolithium reagent is n-butyllithium, and the organic solvent is tetrahydrofuran, 2-methyltetrahydrofuran, n-heptane and methyl tert-butylether.

36. In embodiment 36, the process of embodiment 34 or 35 is wherein the solvent is tetrahydrofuran.

37. In embodiment 37, the process of any one of embodiments 34 to 36, further comprising preparing compound (4):

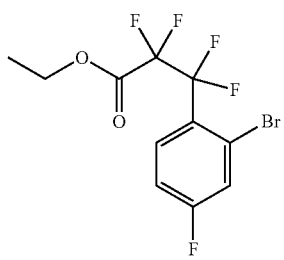

(4)

by treating compound (3):

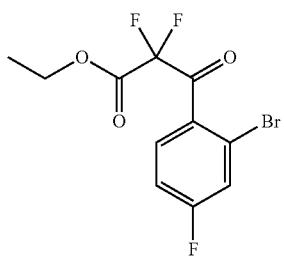

(3)

with a fluorinating agent in a suitable organic solvent.

38. In embodiment 38, the process of claim 37 is wherein the fluorinating agent is diethylaminosulfur trifluoride, 4-tert-butyl-2,6-dimethylphenylsulfur trifluoride, or sulfur tetrafluoride and hydrofluoric acid.

39. In embodiment 39, the process of embodiment 38 is wherein the fluorinating agent is sulfur tetrafluoride and hydrofluoric acid and the solvent is dichloromethane.

40. In embodiment 40, the process of any one of embodiments 37 to 39, further comprising preparing compound (3):

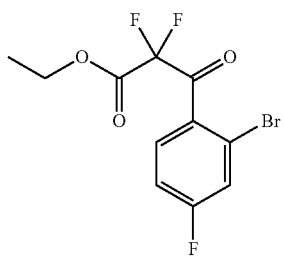

(3)

by treating compound (2):

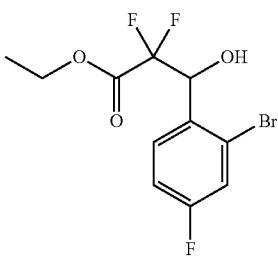

(2)

with an oxidizing agent in a suitable organic solvent.

41. In embodiment 41, the process of embodiment 40 is wherein the oxidizing agent is dimethyl sulfoxide/oxalyl chloride, 2-iodoxybenzoic acid, $RuCl_3/NaBrO_3$, $MnO_2$, $NaBrO_3/NaHSO_3$, or TPAP/NMO.

42. In embodiment 42, the process of embodiment 41 is wherein the oxidizing agent is is TPAP/NMO and reaction is carried in dichloromethane, acetonitrile or tetrahydrofuran, preferably dichloromethane.

42A. In embodiment 42A, the process of embodiment 41 is wherein the oxidizing agent is $RuCl_3/NaBrO_3$.

43. In embodiment 43, the process of any one of embodiments 40 to 42A, further comprising preparing compound (2):

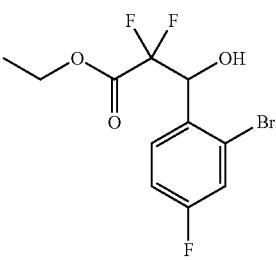

(2)

by treating compound (1):

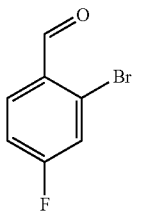

(1)

with ethyl 2-bromo-2,2-difluoroacetate in the presence of zinc metal, trimethylsilyl chloride, and 1,2-dibromoethane in a suitable organic solvent.

44. In embodiment 44, the process of embodiment 43, is wherein the organic solvent is tetrahydrofuran or 2-methyltetrahydrofuran.

EXAMPLES

Abbreviations

ACN: acetonitrile
AcOH or HOAc: acetic acid

AlkylFluor: CAS Registry No. 2043361-32-4
$Cs_2CO_3$: cesium carbonate
DAST: diethylaminosulfur trifluoride
DCM: dichloromethane
HF: hydrofluoric acid
HCl: hydrochloric acid
KOAc: potassium acetate
LDA: lithium diisopropylamide
MTBE: methyl tert-butyl ether
NMO: N-Methylmorpholine N-oxide
MeOH: methanol
$NaBH_4$: sodium borohydride
$NaIO_4$: sodium perodiate
n-BuLi: n-butyllithium
$Pd(PPh_3)_2(OAc)_2$: bis(acetato)bis(triphenylphosphine)palladium(II)
$Pd(PPh_3)_2Cl_2$: bis(triphenylphosphine)palladium(II) dichloride
$Pd_2(dba)_3$: tris(dibenzylideneacetone)dipalladium(0)
PyFluor: 2-pyridinesulfonyl fluoride
$RuCl_3.3H_2O$: ruthenium (III) chloride hydrate
$SF_4$: sulfur tetrafluoride
SulfoxFluor: [methyl(oxo){1-[6-(trifluoromethyl)-3-pyridyl]ethyl}-$\lambda^6$-sulfanylidene]cyanamide
TEMPO: (2,2,6,6-Tetramethylpiperidin-1-yl)oxyl or (2,2,6,6-tetramethylpiperidin-1-yl)oxidanyl
TFA: trifluoroacetic acid
THF: tetrahydronfuran
TPAP: tetrapropylammonium perruthenate
t-BuONa: sodium tert-butoxide
XPhos: 2-dicyclohexylphosphino-2',4',6'-triisopropylbiphenyl Example 1

Synthesis of 2,2,3,3,6-pentafluoro-2,3-dihydro-1H-inden-1-one

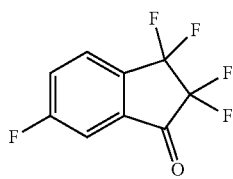 [SMILES: O=C1c2cc(F)ccc2C(F)(F)C1(F)F]

Step 1: ethyl 3-(2-bromo-4-fluorophenyl)-2,2-difluoro-3-hydroxypropanoate

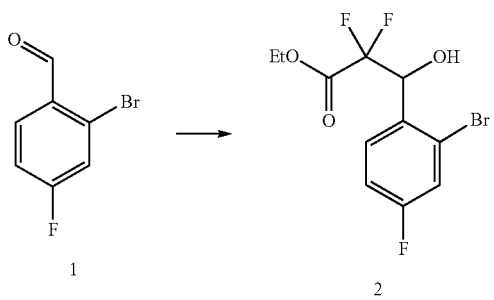 [SMILES: O=Cc1ccc(F)cc1Br ; CCOC(=O)C(F)(F)C(O)c1ccc(F)cc1Br]

To a mixture of zinc (211.36 g, 3.23 mol, 1.31 eq.) in THF (1.50 L) was added 1,2-dibromoethane (13.88 g, 73.89 mmol, 0.030 eq.) and TMSCl (53.52 g, 492.59 mmol, 0.20 eq.) in one portion. The mixture was stirred at 25° C. for 0.5 h, then a solution of 2-bromo-4-fluoro-benzaldehyde (500 g, 2.46 mol, 1.00 eq.) and ethyl 2-bromo-2,2-difluoro-acetate (549.93 g, 2.71 mol, 1.10 eq.) in THF (1.50 L) was added to the mixture dropwise over 1 h under refluxing, and the reaction mixture was stirred continually under refluxing for 1 h. The reaction mixture was cooled, then filtered, and the cake was washed with ethyl acetate. The filtrate was quenched with 1.0 M aqueous HCl (800 mL), then adjusted to pH=5-6 and the mixture was extracted with ethyl acetate. The combined organic phase was washed with 10% brine, dried with $Na_2SO_4$, concentrated in vacuum to give the title compound (857.0 g, 88.8% assay purity, 94.5% assay yield) as a yellow oil, which was used for next step without further purification.

Step 2: ethyl 3-(2-bromo-4-fluorophenyl)-2,2-difluoro-3-oxopropanoate

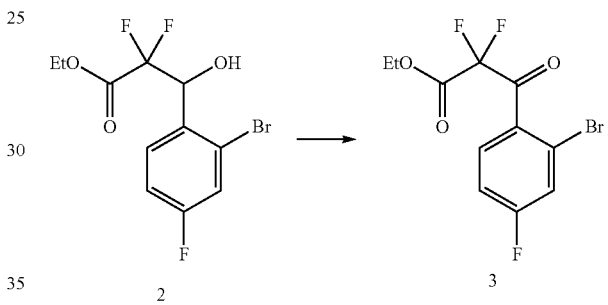

A mixture of NMO (297.86 g, 2.54 mol, 1.40 eq.), TPAP (15.96 g, 45.41 mmol, 0.025 eq.) and 4 Å MS (94.0 g) in DCM (1000 mL) was degassed and purged with $N_2$ and a solution of ethyl 3-(2-bromo-4-fluorophenyl)-2,2-difluoro-3-hydroxypropanoate (669.00 g, 1.82 mol, 88.8% assay, 1.00 eq.) in DCM (1000 mL) was added dropwise at 0-5° C. over 1.5 h. The resulting mixture was further stirred at 25° C. for 2 h under $N_2$ atmosphere, then was filtered through silica gel pad and the pad cake was washed with MTBE. The combined filtrate was washed with 1.0 M aqueous HCl. The combined aqueous phase was extracted with MTBE. The combined MTBE organic phase was washed with $H_2O$, filtered through a silica gel pad and the pad cake was washed with MTBE. The combined filtrate was concentrated to give the title compound (561.0 g, 95.1% yield) as a yellow oil, which was used for next step without further purification.
Alternative Method:
To a stirred mixture of ethyl 3-(2-bromo-4-fluorophenyl)-2,2-difluoro-3-hydroxypropanoate (285.9 g, after assay adjustment, 0.874 mol, 1.00 eq.) in acetonitrile (900 mL) and water (900 mL) were added $NaH_2PO_4$ (63.0 g, 0.525 mol, 0.60 eq.) and $RuCl_3$ (1.81 g, 8.726 mmol, 0.010 eq.) sequentially at 20-30° C. $NaBrO_3$ (158.27 g, 1.049 mol, 1.20 eq.) was then added in portions at 20-30° C. After further stirring at 20-30° C. for 2 h, the reaction mixture was diluted with EtOAc, followed by washing with water, aqueous $Na_2SO_3$, water and then brine. The organic layer was concentrated to obtain the title compound (272.8 g, 95.2% purity, 91.4% yield) as a yellow oil, which was used for next step without further purification.

Step 3: ethyl 3-(2-bromo-4-fluorophenyl)-2,2,3,3-tetrafluoropropanoate

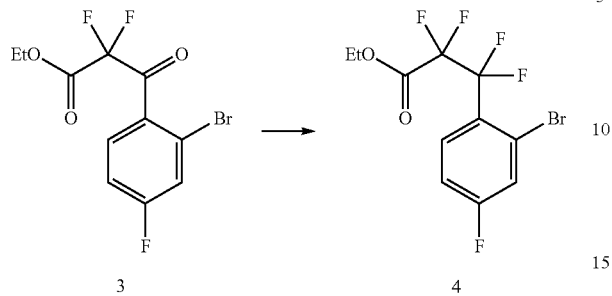

To an autoclave was charged ethyl 3-(2-bromo-4-fluorophenyl)-2,2-difluoro-3-oxopropanoate (550.00 g, 1.69 mol, 1.00 eq.) and DCM (55.5 mL). The mixture was cooled to −78° C. and HF (33.85 g, 1.69 mol, 1.00 eq.) was charged, followed by SF₄ (202.00 g, 1.87 mol, 1.11 eq.). The reaction mixture was warmed to room temperature and stirred at this temperature for 16 h. The reaction mixture was quenched by adding slowly into saturated aqueous Na₂CO₃ (2.5 L), and then extracted with petroleum ether. The combined organic layer was washed with 10% brine, dried over Na₂SO₄, filtered and concentrated. The residue was further purified by vacuum distillation to afford the title compound (474.0 g, 81.1% yield) as yellow oil.

Step 4: 2,2,3,3,6-pentafluoro-2,3-dihydro-1H-inden-1-one

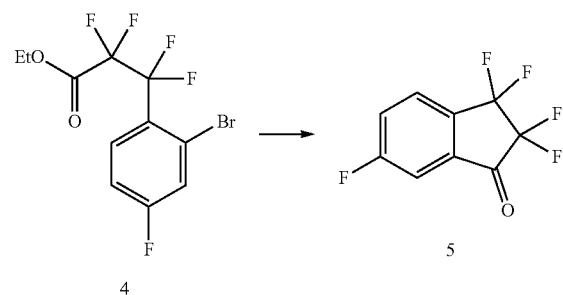 [SMILES: CCOC(=O)C(F)(F)C(F)(F)c1ccc(F)cc1Br ; O=C1c2cc(F)ccc2C(F)(F)C1(F)F]

A stirred solution of ethyl 3-(2-bromo-4-fluorophenyl)-2,2,3,3-tetrafluoropropanoate (100.0 g, 288.11 mol, 1.00 eq.) in THF (1.0 L) was cooled to −65° C., and n-BuLi (2.5 M, 138.0 mL, 345.0 mol, 1.20 eq.) was added dropwise at −60 to −70° C. over 1 h under nitrogen atmosphere. The resulting mixture was stirred further at −65° C. for 1 h, then was quenched with saturated aqueous NH₄Cl at −30 to −40° C., followed by dilution with ethyl acetate and H₂O. After phase separation, the aqueous phase was extracted with ethyl acetate and the combined organic layer was washed with 10% brine, dried over Na₂SO₄, filtered and concentrated to give a residue. The residue was purified by vacuum distillation, and the distillate was triturated with petroleum ether at low temperature to give the title compound (41.0 g, 64.1% yield) as a white solid.

Example 2

Synthesis of (R)-3,3,4,4,7-pentafluoro-2a-hydroxy-2,2a,3,4-tetrahydro-1H-cyclopenta[cd]inden-1-one

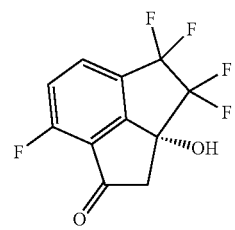 [SMILES: O=C1C[C@@]2(O)c3c(ccc(F)c31)C(F)(F)C2(F)F]

Step 1: (R)-1-allyl-2,2,3,3,6-pentafluoro-2,3-dihydro-1H-inden-1-ol

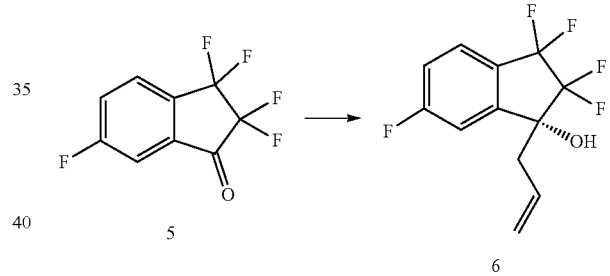

To a dry 3-neck flask were added 2-allyl-4,4,5,5-tetramethyl-1,3,2-dioxaborolane (94.57 g, 562.78 mmol, 1.21 eq.), (S)-2-((3-(tert-butyl)-2-hydroxybenzyl)amino)-N,N,3-trimethylbutanamide (36.51 g, 119.14 mmol, 0.26 eq.), t-BuONa (4.33 g, 45.06 mmol, 0.097 eq.), toluene (900 mL) and MeOH (28.8 g, 898.88 mmol, 1.94 eq.). The mixture was stirred at 20° C. under nitrogen atmosphere until a clear solution formed. The reaction mixture was heated to 60° C., and a solution of 2,2,3,3,6-pentafluoro-2,3-dihydro-1H-inden-1-one (103.09 g, 464.14 mmol, 1.00 eq.) in toluene (100 mL) was added slowly over 2 h at 60° C. The resulting mixture was stirred continually for 16 h at 60° C., then cooled to room temperature, quenched with water, and extracted with MTBE. The organic layer was cooled to 0° C. and washed with 1.0 M aqueous HCl, 0.5 M aqueous NaOH, water and 10% brine. The organic layer was concentrated to give the title compound (146.71 g, 73.5% assay purity, 87.9% assay yield, 90.7% e.e.).

Step 2: (R)-1-allyl-7-bromo-2,2,3,3,6-pentafluoro-2,3-dihydro-1H-inden-1-ol

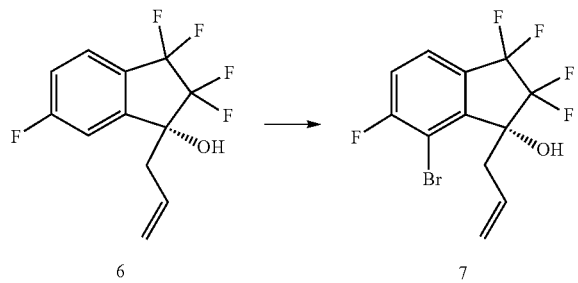 [SMILES: C=CC[C@@]1(O)c2cc(F)ccc2C(F)(F)C1(F)F ; C=CC[C@@]1(O)c2c(ccc(F)c2Br)C(F)(F)C1(F)F]

To a dry 3-neck flask were added THF (500 mL) and LDA (356.82 g, 25%, 832.76 mmol, 2.21 eq.) and then the solution was cooled to −50° C. under nitrogen atmosphere. A solution of (R)-1-allyl-2,2,3,3,6-pentafluoro-2,3-dihydro-1H-inden-1-ol (100.00 g, 378.50 mmol, 1.00 eq.) in THF (200 mL) was added slowly at −50° C. The resulting mixture was stirred at −50° C. for 1 h, then cooled to −80° C. to form solution A.

To another dry 3-neck flask were added 1,2-dibromotetrafluoroethane (196.66 g, 756.91 mmol, 2.00 eq.) and THF (100 mL), and the solution was cooled to −80° C. Solution A was slowly added with stirring and while maintaining the reaction temperature at about −80° C. The mixture was stirred at −80° C. for additional 30 min and then slowly quenched by slowly adding a solution of AcOH (75.00 g, 1248.96 mmol, 3.30 eq.) in THF (75 mL) at temperature below −60° C. The mixture was warmed slowly to room temperature and diluted with water. The mixture was extracted with MTBE, and the combined organic layer was washed with water and 10% brine. The organic layer was concentrated to give the title compound as a solution in THF (204.40 g, 50.4% assay purity, 79.3% assay yield).

Step 3: (R)-3,3,4,4,7-pentafluoro-1-methylene-1,2,3,4-tetrahydro-2aH-cyclopenta[cd]inden-2a-ol

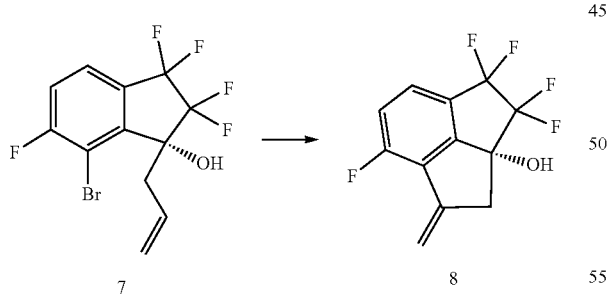

Into a solution of (R)-1-allyl-7-bromo-2,2,3,3,6-pentafluoro-2,3-dihydro-1H-inden-1-ol (100.00 g, 291.47 mmol, 1.00 eq.) in acetonitrile (1.50 L) were added KOAc (86.50 g, 881.39 mmol, 3.03 eq.) and Pd(PPh₃)₂Cl₂ (10.30 g, 14.67 mmol, 0.050 eq.) under N₂ atmosphere. The mixture was stirred for 4 h at 80° C. and then concentrated under vacuum to about 1/3 volume. The residue was diluted with MTBE and washed with water. The organic layer was diluted with n-heptane and passed through a silica gel pad (200 g). The pad was rinsed with MTBE/n-heptane=1/3 to wash out the product. The eluent was concentrated and exchange the solvent into acetonitrile to give the title compound as a solution in acetonitrile (120.15 g, 51.7% assay purity, 81.3% assay yield, 90.6% e.e.).

Step 4: (R)-3,3,4,4,7-pentafluoro-2a-hydroxy-2,2a,3,4-tetrahydro-1H-cyclopenta[cd]inden-1-one

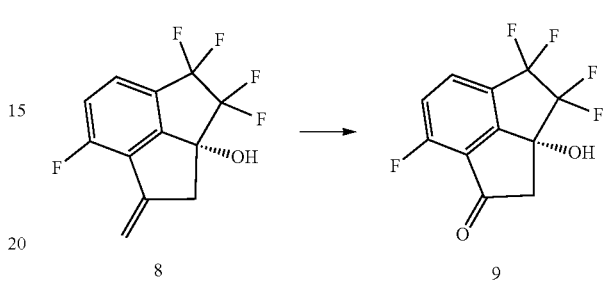

To a stirred mixture of (R)-3,3,4,4,7-pentafluoro-1-methylene-1,2,3,4-tetrahydro-2aH-cyclopenta[cd]inden-2a-ol (80.00 g, 305.13 mmol, 1.00 eq.) in ACN (1200 mL) and H₂O (3200 mL) was added RuCl₃.3H₂O (4.00 g, 15.30 mmol, 0.050 eq.), followed by NaIO₄ (456.87 g, 2.14 mol, 7.01 eq.) in portions while maintaining the reaction temperature at 10 to 20° C. After stirring further at 10 to 20° C. for 1 h, MTBE (800 mL) was added to the mixture and the mixture was filtered through a Celite layer. The Celite solid cake was washed with MTBE. The organic layer was separated from the combined filtrate, and the aqueous layer was extracted with MTBE. The combined organic layer was washed with 5% aqueous Na₂SO₃ and 10% aqueous Na₂SO₄. The organic layer was concentrated, and the residue was dissolved in MTBE and n-heptane. The solution was filtered through a silica gel pad (200 g) and the pad solid cake was rinsed with MTBE/n-heptane=1/3. The combined eluent was concentrated to about 3V to precipitate out the product which was filtered and dried to give the title compound as a white solid (70.62 g, 88.4% assay, 77.5% assay yield, 91.7% e.e.).

Example 3

Synthesis of 3-fluoro-5-((((1R,2aR)-3,3,4,4-tetrafluoro-1,2a-dihydroxy-2,2a,3,4-tetrahydro-1H-cyclopenta[cd]inden-7-yl)oxy)benzonitrile

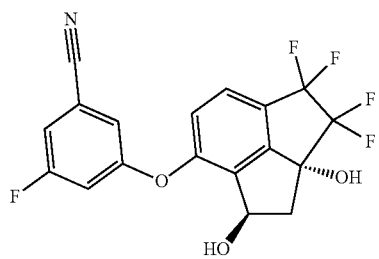 [SMILES: N#Cc1cc(F)cc(Oc2ccc3c4c2[C@H](O)C[C@]4(O)C(F)(F)C3(F)F)c1]

Step 1: (R)-3-fluoro-5-((3,3,4,4-tetrafluoro-2a-hydroxy-1-oxo-2,2a,3,4-tetrahydro-1H-cyclopenta[cd]inden-7-yl)oxy)benzonitrile

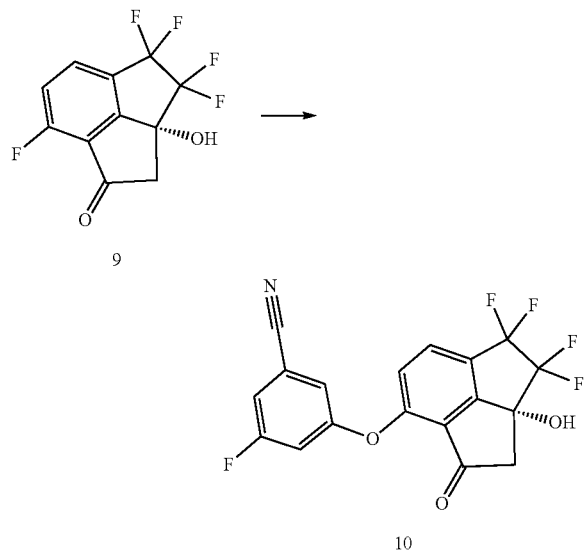 [SMILES: O=C1C[C@@]2(O)c3c(ccc(F)c31)C(F)(F)C2(F)F ; N#Cc1cc(F)cc(Oc2ccc3c4c2C(=O)C[C@]4(O)C(F)(F)C3(F)F)c1]

To a stirred mixture of (R)-3,3,4,4,7-pentafluoro-2a-hydroxy-2,2a,3,4-tetrahydro-1H-cyclopenta[cd]inden-1-one (100.00 g, after assay adjustment, 378.57 mmol, 1.00 eq., 91.7% e.e.) in THF (500 mL) were added 3-fluoro-5-hydroxybenzonitrile (57.10 g, 416.45 mmol, 1.10 eq.) and $Cs_2CO_3$ (74.01 g, 227.15 mmol, 0.60 eq.) at room temperature. The resulting mixture was stirred at 40° C. for 20 h. The mixture was cooled to room temperature and MTBE was added, followed by water. After layer separation, the aqueous layer was extracted with MTBE and the combined organic layer was washed with 5% aqueous $Na_2CO_3$ and then 10% brine. The organic layer was concentrated and the residue was recrystallized from MTBE/n-heptane=3/20 to give the title compound as a yellow solid (145.78 g, 84.4% assay purity, 85.2% assay yield, 98.4% e.e.).

Step 2: 3-fluoro-5-(((1R,2aR)-3,3,4,4-tetrafluoro-1,2a-dihydroxy-2,2a,3,4-tetrahydro-1H-cyclopenta[cd]inden-7-yl)oxy)benzonitrile

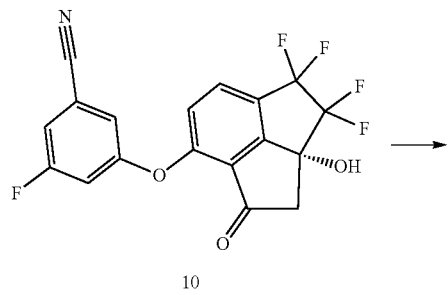

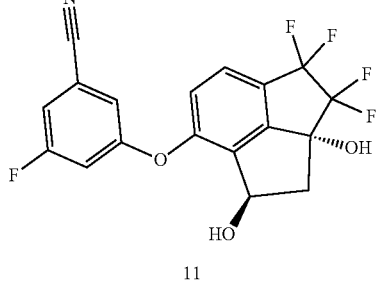

To a stirred solution of (R)-3-fluoro-5-((3,3,4,4-tetrafluoro-2a-hydroxy-1-oxo-2,2a,3,4-tetrahydro-1H-cyclopenta[cd]inden-7-yl)oxy)benzonitrile (50.00 g, after assay adjustment, 131.14 mmol, 1.00 eq., 98.4% e.e.) in MeOH (53.0 mL, 1.31 mol, 10.00 eq.) and THF (500 mL) was added $NaBH_4$ (1.84 g, 48.64 mmol, 0.37 eq.) in portions at −5 to 0° C. The reaction mixture was stirred at −5 to 0° C. for an additional hour, then quenched with 2.0 M aqueous HCl (about 30.0 g) below 5° C. to pH=5-7 and diluted with water. The mixture was extracted with MTBE, and the combined organic layer was washed with water and 10% brine. The organic layer was concentrated, and the solvent was exchanged to THF to obtain a THF solution of the title compound (286.66 g, 16.6% assay purity, 94.7% assay yield, 97.7% e.e.). $^1$H NMR (400 MHz, $CDCl_3$) δ=7.55 (d, 1H), 7.18-7.16 (m, 2H), 7.13 (d, 1H), 7.08 (d, 1H), 5.89-5.84 (m, 1H), 3.06 (s, 1H), 2.83-2.78 (m, 1H), 2.47-2.42 (m, 1H), 2.35 (d, 1H).

What is claimed:

1. A process of preparing compound (11):

(11)

comprising reducing the keto moiety of compound (10):

(10)

with a suitable reducing agent in a suitable organic solvent and optionally in the presence of an organic acid.

2. The process of claim 1, wherein the reducing agent is sodium borohydride, lithium borohydride, sodium acetoxy borohydride, or sodium cyanoborohydride.

3. The process of claim 1, wherein the reduction of the keto moiety of compound (10) is carried out with sodium borohydride in tetrahydrofuran, 2-methyltetrahydrofuran, a mixture of tetrahydrofuran or 2-methyltetrahydrofuran and methanol, tetrahydrofuran containing acetic acid or trifluoroacetic acid, 2-methyltetrahydrofuran containing acetic acid or trifluoroacetic acid, or methanol containing acetic acid or trifluoroacetic acid.

4. The process of claim 3, wherein the reduction of the keto moiety of compound (10) is carried out in a mixture of tetrahydrofuran and methanol and the reaction is carried out at about −5° C. to about 30° C.

5. A process of preparing compound (10):

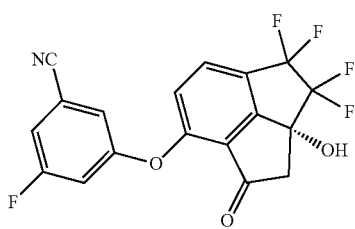
(10)

comprising reacting compound (9):

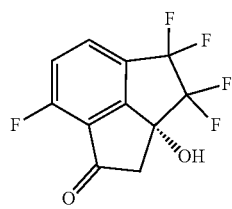
(9)

with 3-fluoro-5-hydroxybenzonitrile in the presence of a base in a suitable organic solvent.

6. The process of claim 1, further comprising preparing compound (10):

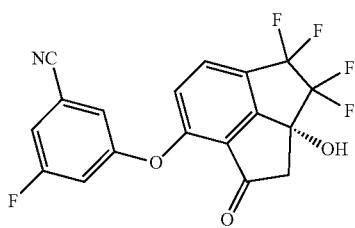
(10)

by reacting compound (9):

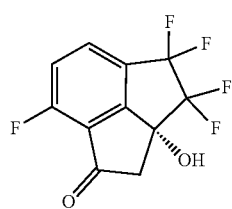
(9)

with 3-fluoro-5-hydroxybenzonitrile in the presence of a base in a suitable organic solvent.

7. The process of claim 5, wherein the base is an inorganic base.

8. The process of claim 6, wherein the base is an inorganic base.

9. The process of claim 6, wherein the base is cesium carbonate or potassium carbonate, and the organic solvent is tetrahydrofuran, 2-methyltetrahydrofuran, dimethylformamide, acetonitrile, or toluene.

10. The process of claim 9, further comprising crystallizing compound (10) from a mixture of an ether and an alkane solvent.

11. The process of claim 10, wherein compound (10) is crystallized from a mixture of methyl tert-butyl ether and n-heptane.

12. A process for preparing compound (9):

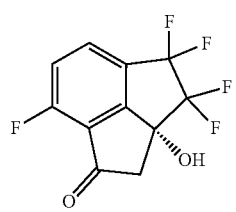
(9)

comprising carrying out oxidative cleavage of the vinylidene moiety of compound (8):

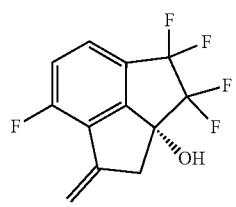
(8)

with a suitable oxidizing agent in a suitable organic or aqueous organic solvent.

13. The process of claim 12, wherein the oxidative cleavage of the vinylidene moiety of compound (8) is carried out with (i) sodium periodate in the presence of ruthenium chloride in aqueous acetonitrile, (ii) Oxone in the presence of ruthenium chloride in a suitable organic or aqueous organic solvent, or (iii) Ozone in a suitable organic or aqueous organic solvent.

14. The process of claim 5, further comprising preparing compound (9):

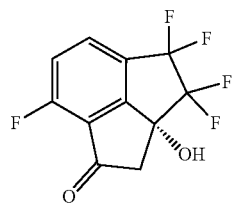
(9)

by carrying out oxidative cleavage of the vinylidene moiety of compound (8):

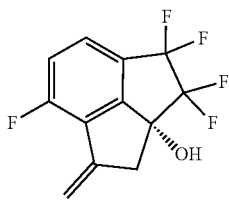
(8)

with a suitable oxidizing agent in a suitable organic or aqueous organic solvent.

15. The process of claim 9, further comprising preparing compound (9):

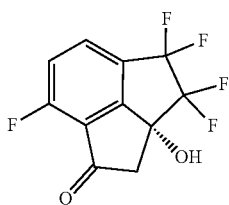
(9)

by carrying out oxidative cleavage of the vinylidene moiety of compound (8):

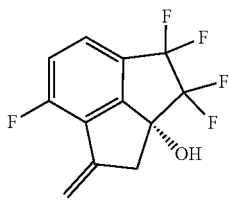
(8)

with a suitable oxidizing agent in a suitable organic or aqueous organic solvent.

16. The process of claim 15, wherein the oxidative cleavage of the vinylidene is carried out with (i) sodium periodate or Oxone in the presence of ruthenium chloride or (ii) Ozone.

17. The process of claim 15, wherein the oxidative cleavage of the vinylidene is carried out with sodium periodate in the presence of catalytic amount of ruthenium chloride in aqueous acetonitrile.

18. A process for preparing compound (8):

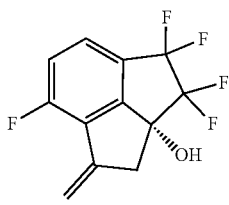
(8)

comprising performing intramolecular cyclization between the alkene and bromo groups in compound (7):

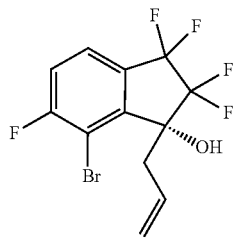
(7)

by treating compound (7) with a palladium catalyst in the presence of a base in a suitable organic or aqueous organic solvent.

19. The process of claim 18, wherein the palladium catalyst is Pd(PPh$_3$)$_4$, Pd(dppf)Cl$_2$, Pd(PPh$_3$)$_2$Cl$_2$, Pd(PPh$_3$)$_2$ (OAc)$_2$, Pd$_2$(dba)$_3$/XPhos, or Pd(1,2-bis(diphenylphosphino)-ethane)(OAc)$_2$, and the organic solvent is acetonitrile, tetrahydrofuran, 2-methyltetrahydrofuran, toluene, 1,4-dioxane, or dimethylformamide.

20. The process of claim 16, further comprising preparing compound (8):

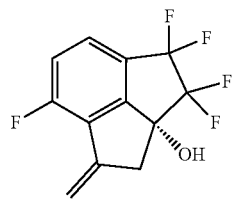
(8)

by performing intramolecular cyclization between the alkene and bromo groups in compound (7):

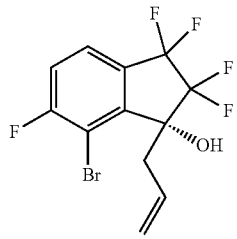
(7)

with a palladium catalyst in the presence of a base in a suitable organic solvent.

21. The process of claim 20, wherein the palladium catalyst is Pd(PPh$_3$)$_4$, Pd(dppf)Cl$_2$, Pd(PPh$_3$)$_2$Cl$_2$, Pd(PPh$_3$)$_2$ (OAc)$_2$, Pd$_2$(dba)$_3$/XPhos, or Pd(1,2-bis(diphenylphosphino)-ethane)(OAc)$_2$, and the organic solvent is acetonitrile, tetrahydrofuran, 2-methyltetrahydrofuran, toluene, 1,4-dioxane, or dimethylformamide.

22. The process of claim 21, wherein the base is sodium acetate, potassium acetate, sodium carbonate, potassium carbonate, or cesium carbonate.

23. The process of claim 20, wherein the palladium catalyst is Pd(PPh$_3$)$_2$Cl$_2$, the base is potassium acetate, and the solvent is acetonitrile.

24. A process for preparing compound (7):

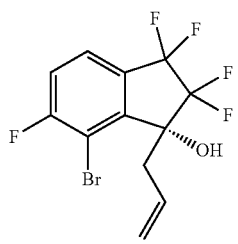

(7)

comprising brominating compound (6):

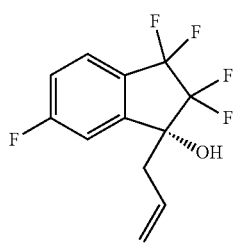

(6)

with a brominating agent in the presence of a deprotonating agent in a suitable organic solvent.

25. The process of claim 24, wherein compound (6) is brominated with 1,2-dibromo-1,1,2,2-tetrafluoroethane in the presence of a deprotonating agent in a suitable organic solvent.

26. The process of claim 21, further comprising preparing compound (7):

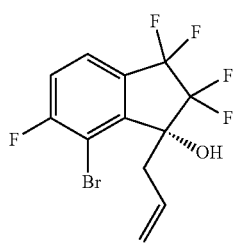

(7)

by treating compound (6):

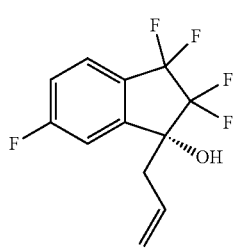

(6)

with a brominating agent in the presence of a deprotonating agent in a suitable organic solvent.

27. The process of claim 26, wherein the brominating agent is carbon tetrabromide or 1,2-dibromo-1,1,2,2-tetrafluoroethane.

28. The process of claim 26 wherein the brominating agent is 1,2-dibromo-1,1,2,2-tetrafluoroethane, the deprotonating agent is lithium diisopropylamide, and the solvent is tetrahydrofuran.

29. The process of claim 26, further comprising preparing compound (6):

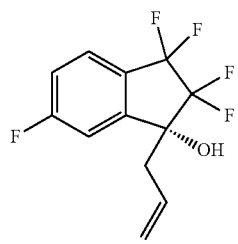

(6)

by treating compound (5):

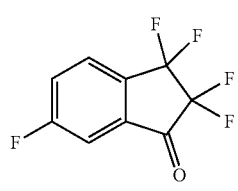

(5)

with 4,4,5,5-tetramethyl-2-(prop-2-en-1-yl)-1,3,2-dioxaborolane in the presence of (S)-2-((3-(tert-butyl)-2-hydroxybenzyl)amino)-N,N,3-trimethylbutanamide and a base in a suitable organic solvent.

30. The process of claim 29, wherein the base is sodium tert-butoxide and the organic solvent is a mixture of methanol and toluene.

31. The process of claim 29, further comprising preparing compound (5):

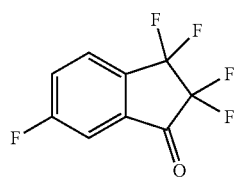

(5)

by treating compound (4):

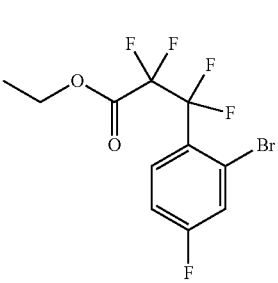

(4)

with an organolithium reagent in a suitable organic solvent.

32. The process of claim 31, wherein the organolithium reagent is n-butyllithium and the organic solvent is tetrahydrofuran, 2-methyltetrahydrofuran, n-heptane, or methyl tert-butylether.

33. The process of claim 31, further comprising preparing compound (4):

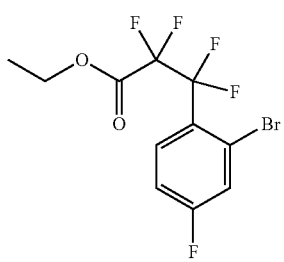
(4)

by treating compound (3):

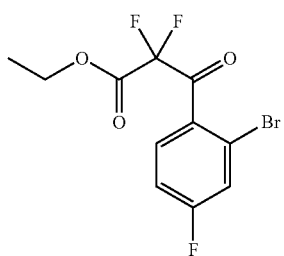
(3)

with a fluorinating agent in a suitable organic solvent.

34. The process of claim 32, wherein the fluorinating agent is diethylaminosulfur trifluoride, 4-tert-butyl-2,6-dimethylphenylsulfur trifluoride, or sulfur tetrafluoride and hydrofluoric acid.

35. The process of claim 33, further comprising preparing compound (3):

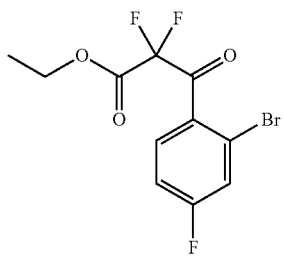
(3)

by treating compound (2):

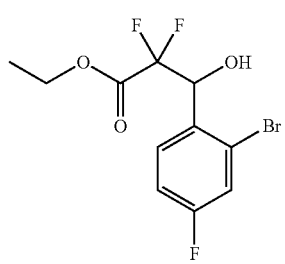
(2)

with an oxidizing agent in a suitable organic solvent.

36. The process of claim 35, wherein the oxidizing agent is dimethyl sulfoxide/oxalyl chloride, 2-iodoxybenzoic acid, $RuCl_3/NaBrO_3$, $MnO_2$, $NaBrO_3/NaHSO_3$, or TPAP/NMO.

37. The process of claim 35, further comprising preparing compound (2):

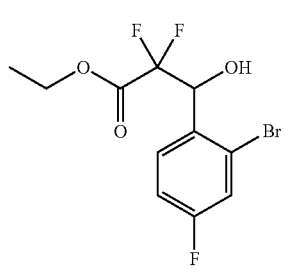
(2)

by treating compound (1):

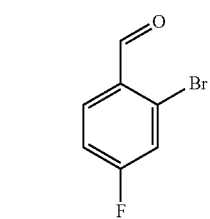
(1)

with ethyl 2-bromo-2,2-difluoroacetate in the presence of zinc metal, trimethylsilyl chloride, and 1,2-dibromoethane in a suitable organic solvent.

* * * * *

UNITED STATES PATENT AND TRADEMARK OFFICE
CERTIFICATE OF CORRECTION

PATENT NO. : 11,634,382 B2
APPLICATION NO. : 17/503176
DATED : April 25, 2023
INVENTOR(S) : Jiping Fu et al.

Page 1 of 1

It is certified that error appears in the above-identified patent and that said Letters Patent is hereby corrected as shown below:

On the Title Page

Please add the Foreign Application Priority Data:
[30] October 19, 2020 [CN] China......................PCT/CN2020/121780

In the Specification

In Column 9, Line 36, the term "an/or" should be corrected to --and/or--.

In Column 11, Line 3, the term "TPAP/NMO." should be corrected to --TPAP/NMO;--.

In Column 18, Line 4, the term "at out at" should be corrected to --at out--.

In Column 19, Line 44, the term "claim" should be corrected to --embodiment--.

In Column 20, Line 21, the term "is is" should be corrected to --is--.

In Column 21, Line 14, the term "perodiate" should be corrected to --periodiate--.

Signed and Sealed this
First Day of April, 2025

Coke Morgan Stewart
*Acting Director of the United States Patent and Trademark Office*